(12) United States Patent
Cai et al.

(10) Patent No.: US 7,975,341 B2
(45) Date of Patent: Jul. 12, 2011

(54) BIO-ACTIVATED ORAL CARE INSTRUMENT

(75) Inventors: Heng Cai, Skillman, NJ (US); Thomas James Boyd, Metuchen, NJ (US)

(73) Assignee: Colgate-Palmolive Company, New York, NY (US)

(*) Notice: Subject to any disclaimer, the term of this patent is extended or adjusted under 35 U.S.C. 154(b) by 843 days.

(21) Appl. No.: 11/866,078

(22) Filed: Oct. 2, 2007

(65) Prior Publication Data
US 2009/0087813 A1 Apr. 2, 2009

(51) Int. Cl.
  A46B 11/00 (2006.01)
  A46B 13/02 (2006.01)
  A46B 13/04 (2006.01)
  A61C 17/02 (2006.01)
  A61C 17/22 (2006.01)

(52) U.S. Cl. ............ 15/22.1; 15/28; 15/29; 200/61.05; 401/268; 433/27; 433/99; 433/100; 601/162

(58) Field of Classification Search .......... 15/22.1–22.4, 15/23, 24, 28, 29; 200/61.04–61.07; 401/188 R, 401/195, 268, 292; 433/27, 98–100; 601/162–165
See application file for complete search history.

(56) References Cited

U.S. PATENT DOCUMENTS

| | | | |
|---|---|---|---|
| 3,106,732 A | 10/1963 | Dayton et al. | |
| 3,478,741 A | 11/1969 | Simor | |
| 3,520,297 A | 7/1970 | Bechtold | |
| 3,749,885 A * | 7/1973 | Nagasima | 219/522 |
| 4,882,801 A | 11/1989 | Benz | |
| 4,969,868 A | 11/1990 | Wang | |
| 5,427,870 A | 6/1995 | Joshi et al. | |
| 5,567,287 A | 10/1996 | Joshi et al. | |
| 6,045,055 A | 4/2000 | Joshi et al. | |
| 6,135,126 A | 10/2000 | Joshi | |
| 6,233,773 B1 * | 5/2001 | Karge et al. | 15/29 |
| 6,341,400 B1 | 1/2002 | Kobayashi et al. | |
| 6,575,961 B2 | 6/2003 | Joshi | |
| 6,743,015 B2 | 6/2004 | Magnani | |
| 6,792,640 B2 | 9/2004 | Lev | |
| 6,802,097 B2 * | 10/2004 | Hafliger et al. | 15/22.1 |
| 6,895,625 B2 | 5/2005 | Lev et al. | |
| 6,902,397 B2 | 6/2005 | Farrell et al. | |
| 6,918,153 B2 * | 7/2005 | Gruber | 15/22.1 |
| 6,952,855 B2 | 10/2005 | Lev et al. | |
| 7,080,980 B2 * | 7/2006 | Klupt | 433/80 |
| 2005/0023371 A1 | 2/2005 | Joshi et al. | |
| 2005/0129453 A1 * | 6/2005 | Bravo-Loubriel | 401/188 R |
| 2007/0154863 A1 | 7/2007 | Cai et al. | |
| 2008/0060148 A1 * | 3/2008 | Pinyayev et al. | 15/22.1 |

FOREIGN PATENT DOCUMENTS

DE   101 01 163 A1   7/2002

(Continued)

OTHER PUBLICATIONS

International Search Report Dated Dec. 16, 2008.

*Primary Examiner* — Mark Spisich
(74) *Attorney, Agent, or Firm* — Judy W. Chung

(57) ABSTRACT

An oral care instrument, such as a motorized toothbrush, which activates upon exposure to the oral environment of the user, is described. The electrical conductivity of saliva, optionally mixed with toothpaste and water, may be utilized to complete an electrical circuit that powers a motorized device within the instrument.

20 Claims, 1 Drawing Sheet

FOREIGN PATENT DOCUMENTS

| | | |
|---|---|---|
| DE | 102 24 043 A1 | 12/2003 |
| GB | 2 030 855 A | 4/1980 |
| GB | 2317555 | 12/2000 |
| JP | 02277407 | 11/1990 |
| JP | 08 275961 A | 10/1996 |
| JP | 10042962 | 2/1998 |

* cited by examiner

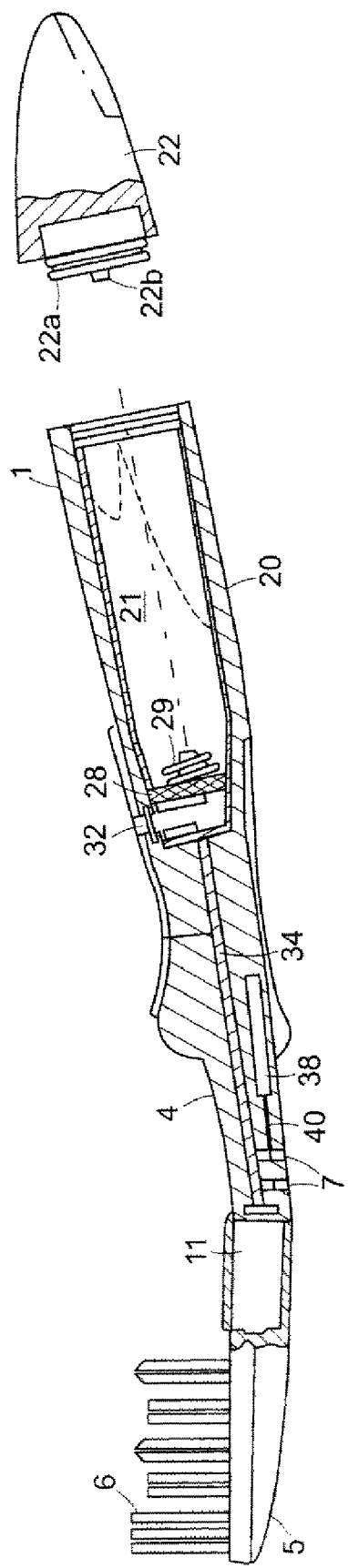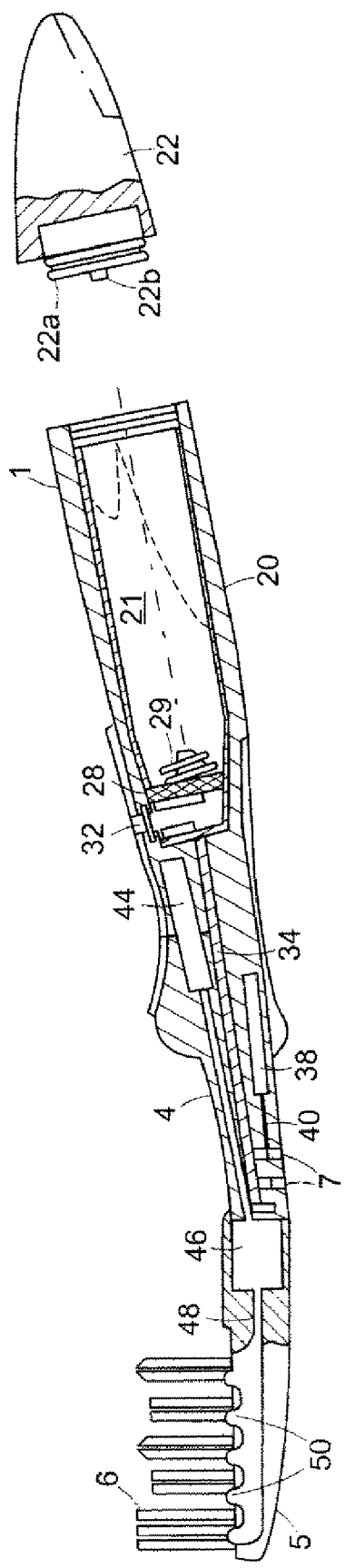

BIO-ACTIVATED ORAL CARE INSTRUMENT

FIELD OF THE INVENTION

The present invention pertains to an oral care instrument, such as a motorized toothbrush, which activates upon exposure to the oral environment of the user.

BACKGROUND OF THE INVENTION

Powered oral care instruments such as electric, motorized toothbrushes used to clean teeth are well known. Typically these toothbrushes employ vibrating or rotating motion, or a combination of motions, to effectuate tooth cleaning, whitening, and/or repair. Toothbrushes may also include a motorized activator, such as a pump, for dispensing active agents to one or more outlets.

A feature commonly found on electric toothbrushes and other oral care instruments is an on/off switch or button which may be shifted or depressed to electrically activate or deactivate the instrument.

In the case of an electric toothbrush, for example, activation establishes an electrical circuit which causes movement of the bristles for contacting tooth and soft tissue surfaces, or dispensing of an active agent. The switch is typically located on or near the handle portion of the toothbrush. The primary feature of such a switch is that it remains either in the "on" position or the "off" position until the user manually changes it. The toothbrush motor can be engaged or activated prior to the brush head being placed in the mouth, or the user can wait until the brush head is placed within the mouth before activating the motor.

It would be desirable to provide a toothbrush that reduces or overcomes some or all of the difficulties inherent in prior known toothbrushes. Particular objects and advantages will be apparent to those skilled in the art, that is, those who are knowledgeable or experienced in this field of technology, in view of the following disclosure of the invention and detailed description of certain embodiments.

SUMMARY

Aspects of the present invention advantageously exploit particular conditions which are present in the mouth, either continually or at discreet instances during oral care or treatment. The electrical conductivity of saliva, optionally mixed with toothpaste and water, may be utilized to activate or complete an electrical circuit that powers the instrument. The existence of one or more such conditions provides a basis for automatic functioning of the oral care instrument when a portion (e.g., the head, or the head and neck) is placed into the mouth and the condition, or a combination of conditions, is/are detected.

In accordance with one aspect, a motorized toothbrush includes a head carrying cleaning elements and a handle configured to connect to a power source. A motorized device is activated upon exposure of the toothbrush to an electrolyte solution.

In accordance with another aspect, a motorized toothbrush includes a head carrying cleaning elements, a handle including a cavity, and a power source received in the cavity of the handle. A motorized device is operably connected to the power source and operably connected to the head. Electrical conducting elements are operably connected to the power source and the motorized device. The motorized device is activated upon exposure of the electrical conducting elements to an electrolyte solution.

In accordance with a further aspect a motorized toothbrush includes a head carrying cleaning elements, a handle, and a power source contained within the handle. A motorized device is operably connected to the power source and operably connected to the head. Electrical conducting elements are operably connected to the power source and the motorized device. A switch is operably connected to at least one of the electrical conducting elements and the power source. The motorized device is activated upon exposure of the electrical conducting elements to an electrolyte solution having a threshold conductivity.

These and other aspects of the invention are apparent from the following detailed description of certain embodiments.

BRIEF DESCRIPTION OF THE DRAWINGS

The drawings should be understood to present an illustration of various aspects of the invention and/or principles involved, and not to limit the scope of the subject matter as set forth in the appended claims.

FIG. 1 depicts a representative oral care instrument, a toothbrush, illustrating various aspects of the invention.

FIG. 2 depicts an alternative embodiment of a toothbrush illustrating various aspects of the invention.

DETAILED DESCRIPTION OF CERTAIN PREFERRED EMBODIMENTS

The present invention relates to a bio-active oral care instrument, having the ability to operate automatically, when the instrument or a portion thereof is exposed to one or more conditions, such as the ambient electrical conductivity, existing in the oral environment. Other conditions and combinations of conditions, such as pH, temperature, solute concentrations, etc. could likewise be detected and used as the basis for automatic operation. Furthermore, aspects of the invention are illustrated in the remainder of this disclosure with reference to an electric motorized toothbrush, although it is understood that the operation of any number of oral care instruments, together with the associated advantageous features and/or beneficial effects described herein, could likewise be achieved. Other oral care instruments, for example, include those used in dental drilling, polishing, and grinding; oral suction instruments, oral surgical instruments; and other instruments used in the oral cavity which are powered by motorized devices and especially electrical devices.

The representative toothbrush illustrated in FIG. 1 has a handle 1 and a head 5 carrying one or more cleaning elements, which are depicted in FIG. 1 as a plurality of bristles 6. Also illustrated is a neck 4 located between, and connecting, handle 1 and head 5. The bristles 6, as shown, form clusters that are anchored to the head 5 and provide a profiled brushing surface with their free ends. Other bristle configurations are of course possible, as well as removable/exchangeable bristle clusters. Different types of cleaning elements (e.g., elastomeric wipers, nodules, pointed structures, etc.) may also be carried on head 5 instead of, or in addition to, bristles.

The neck 4 is provided with electrical conducting elements 7 (e.g., an anode and a cathode) that are exposed to the exterior surface of the toothbrush. In other embodiments, the electrical conducting elements 7 can be located on the head 5, for example on the surface opposite that which carries bristles 6. The use of electrical conducting elements 7 on different parts of the toothbrush is also possible. A plurality of electrical conducting elements 7 can also be incorporated in various positions to activate the instrument in the event that sufficient electrical conductivity is established between any given pair(s) of electrical conducting elements 7 located at any desired position. Integrated in the region of the neck 4 which is adjacent to the head 5 is a motorized device 11 such as a mechanical vibratory device. Motorized device 11 is operably connected to head 5 such that vibrations or other movement produced by motorized device 11 may be imparted to the head 5 and/or the bristles 6 to effect or enhance the teeth-cleaning or teeth-whitening action. The motorized device 11 is operably connected, via electrical connections 34 in the neck 4 to a power source (e.g., a battery, not shown), which may be accommodated in the handle 1. Operably connected and operably connectable refer to the ability of the electrical connections, or other elements, to readily form an electrical circuit (e.g., when a switch is depressed or when a power source is connected or installed). Operably connected and operably connectable may also refer to the ability of mechanical components to be connected to one another in such a manner as to allow or provide for physical movement of one or more elements. The motorized device may be alternatively incorporated in the head 5 or handle 1 of the toothbrush. In representative embodiments, electrical connections 34 may be metal wire or electrically conductive plastic tracks.

In a particular embodiment where motorized device 11 is a vibratory device, it will have a vibratory element which can be in the form of an eccentric, which produces mechanical vibrations and can be rotated about an axis located in the longitudinal direction of the toothbrush. Alternatively, instead of an eccentric which can be driven in rotation, it would also be possible to have a vibratory element which can be driven in a translational manner. Otherwise, the bristle-carrying head 5 can be arranged such that it can be moved in relation to the neck 4 in order for the latter, in the case of vibrations produced by motorized device 11, to move in relation to the rest of the toothbrush.

As shown, also accommodated in the handle 1 is a sheath or sleeve 20 which extends in the longitudinal direction of the handle 1 and is made of electrically conductive material. In the representative embodiment shown, both the handle 1 and the sleeve 20 are open to the rear, thus forming a cavity 21 which can be closed from the rear by a closure part 22 and into which it is possible to insert a battery, such as a commercially available, non-rechargeable cylindrical battery, with a defined voltage (e.g. 1.5V), as the power or voltage source for motorized device 11. It would also be possible, however, for a button cell or for a rechargeable storage batter to be used as the power source. An external power source such as a conventional electrical outlet or a combination of voltage sources may be employed as the power source.

Also shown in the particular illustrative embodiment of FIG. 1 is a spring contact 29 for a positive pole of a battery (not shown), which is fitted in the sleeve 20, on a transverse wall 2S, and is electrically connected to the motorized device 11 through the electrical connections 34 and switch 32, which is installed in the sleeve 20 and can be actuated from the outside of the handle 1. Switch 32 may also be, for example, a magnetic switch pulse switch or a pulse switch arranged on a printed circuit board with further electronic components that store the switching state. In other embodiments, closure part 22 can itself act as a switch, such that electrical contact between the power source and motorized device 11 is established or interrupted by turning closure part 22 to alter the position of contact surface 22b relative to the negative pole of a battery.

It is to be appreciated, as discussed in greater detail below, that switch 32 is not necessary due to the ability of the toothbrush to turn on automatically when in the user's mouth. In some embodiments, therefore, the toothbrush can be "switchless" or "buttonless."

Switch 32 may be depressed or adjusted by the user to effect a number of operating modes. For example, in "on" and "off" positions or settings, electrical communication or an electrical circuit between the power source and motorized device 11 may be continually established or continually interrupted, respectively. In the former case, for example, the electrical conducting elements 7 may be bypassed to allow continuous operation of motorized device 11, regardless of the presence of a conductive medium between electrical conducting elements 7. Switch 32 may also have a position corresponding to conditional completion of the electrical circuit.

Also as shown in FIG. 1, the closure part 22 is provided with a threaded stub 22a made of an electrically conductive material, which may be the same material (e.g., a metal such as copper or a conductive plastic) used for the electrical conducting elements 7, electrical connections 34, spring contact 29, and/or sleeve 20. Closure part 22 can be screwed into the handle 1 and/or into the sleeve 20 by way of said threaded stub 22a. The threaded stub 22a is provided with a contact surface 22b which, with the closure part 22 screwed in, comes into abutment against the negative pole of a battery (not shown) when inserted into the sleeve 20. During operation of the motorized toothbrush, this negative pole is electrically connected to motorized device 11 via the threaded stub 22a, the sleeve 20 itself, and electrical connections 34 connecting sleeve 20 to motorized device 11. It would also be possible, instead of through the use of sleeve 20, for the power from the negative pole to be transmitted in some other way, for example using wires or electrically conductive plastic tracks. Instead of the rear closure part 22 being screwed to the handle 1, it would, of course, also be possible to have some other type of releasable connection (e.g. plug-in connection, bayonet connection, etc.) and a corresponding configuration of the contact part interacting with the negative pole of the battery.

One representative characteristic of the oral environment which differs significantly from the surrounding or ambient "non-use" environment is electrical conductivity, which increases directionally with the concentration of electrolytes in the surrounding medium (e.g., saliva). In some embodiments, this "non-use" environment may even include rinsing or submersing the portion of the instrument that is normally placed in the mouth (e.g., the head 5 of the toothbrush) in water (e.g., for pre-wetting or rinsing purposes), since the electrical conductivity of saliva is higher than that of water. This difference can thus be utilized to allow the instrument to "detect" when it is being used and thereby operate in an automatic mode.

Additionally, the combination of water, saliva, and dentifrice (e.g., toothpaste or other ingredient that is generated in the mouth during use of the instrument often affords even a significantly higher electrical conductivity than saliva alone. This is due to the generation of ions, often in large concentrations, from typical oral care products, including tooth fluoridating, whitening, and/or remineralization products which contain or form aqueous cations, such as sodium ($Na^+$), potassium ($K^+$), calcium ($Ca^{+2}$), magnesium ($Mg^{+2}$), iron ($Fe^{+3}$), etc. and anions, such as phosphate ($PO_4^{-3}$), diphosphate ($P_2O_7^{-4}$), carbonate ($CO_3^{-2}$), fluoride ($F^-$), chloride ($Cl^-$), etc.

In view of the above, the increase in electrical conductivity surrounding a portion of the toothbrush, e.g., head 5 or head 5 and neck 4, when placed in the mouth, can be used to complete an electrical circuit, together with an electrical power or voltage source such as an external electrical outlet or an internal battery to activate motorized device 11, causing movement of head 5.

In an "auto" position or setting, motorized device 1 is powered by the power source only in the event that sufficient electrical conductivity (e.g., a threshold level of conductivity, or sufficiently low resistance) exists between electrical conducting elements 7 in the neck 4. The required electrical conductivity, as needed for the "conditional completion" of the electrical circuit to power motorized device it, may be provided, for example, by an electrolyte solution containing ions (e.g., calcium, phosphate, fluoride, or peroxide ions) such as that generated from a combination of saliva, water, and toothpaste existing in the oral environment during use. When the electrical conductivity between conducting elements 7 is no longer present, the electrical circuit is incomplete, thereby deactivating motorized device 11. Thus, in an "auto" or automatic operating mode, motorized device 11 will not be activated when the toothbrush is stored since air is the medium between electrical conducting elements 7. According to some embodiments, when the brush is being rinsed outside the mouth, the water between electrical conducting elements 7 will not have sufficient electrical conductivity to activate motorized device 11.

According to some embodiments of the invention, it may be desired to require that the electrolyte solution (e.g., saliva or a water/saliva/toothpaste mixture), to which the toothbrush is exposed during use, have a threshold (or minimum) level of conductivity before motorized device 11 is activated. This threshold level of conductivity, for example, may be based on a threshold (or minimum) current needed to activate motorized device 11. This threshold conductivity, required to automatically turn on the toothbrush, may be associated with the electrical conductivity of saliva alone or an electrolyte solution having a relatively higher conductivity (e.g., an aqueous solution of toothpaste) or lower (e.g., a mixture of saliva and water) conductivity. For example, the threshold conductivity may be associated with a standard or model electrolyte solution designed to mimic the electrical conductivity of saliva having one or more specified, additional concentrations of dissolved ions such as calcium phosphate, fluoride, peroxide, and other ions or mixtures of ions.

In this manner, the automatic functioning of the oral care instrument can be made more or less sensitive to the particular conditions or conditions associated with the environment in which the instrument is used (i.e., the "use" condition(s) required to activate the instrument). It is also possible that the sensitivity of the instrument can be adjusted by, set by, or tailored to, the user (e.g., to avoid either activation of the instrument during "non-use" conditions or non-activation during "use" conditions) and thereby ensure effective functioning of the instrument in automatic mode.

In certain embodiments, the change in conductivity of the medium between electrical conducting elements 7 is measured by a sensing device 38, such as a circuit board 38 or other suitable sensing device, connected to electrical conducting elements 7 by electrical connections 40. In certain embodiments, sensing device 38 may measure the drop in resistance between conducting elements 7. When the conductivity change reaches a preset value as detected by sensing device 38, switch 32 may be activated so as to complete the electrical circuit to power motorized device 11. In such an embodiment, the electrical circuit need not include the electrolyte solution between conducting elements 7. That is, the electrolyte solution is used as a trigger to activate switch 32 by way of sensing device 38, but does not actually form part of the electrical circuit that powers motorized device 11.

In other embodiments, switch 32 could be activated based on the differential change in conductivity between conducting elements 7. It is to be appreciated that the level of electrolyte in the medium will vary from person to person, and/or may vary based on the formula of the oral care solution used. In such embodiments, these variations will not affect the current level delivered to the motor. Thus, for example, when using a sensitivity type toothpaste product having 5% $KNO_3$, the toothbrush would not operate differently than when used with a standard toothpaste product having a lower ionic strength.

According to other embodiments, when exposed to a solution with a threshold level of electrical conductivity, motorized device 11 and, therefore, the dental instrument itself may be set or adjusted (e.g., using a timer) to activate for a minimum duration (e.g., a typical brushing duration such as about 1 minute to about 5 minutes). This ensures that the toothbrush or other instrument will function for at least enough time to effectively accomplish a given task (e.g., tooth cleaning and/or whitening). This also promotes continuous operation, even if contact between the instrument and the electrolyte solution is temporarily lost, for example, when a toothbrush is temporarily removed from the mouth during brushing. The minimum duration for activation of the dental instrument (e.g., two minutes) may be fixed or may otherwise be set or adjusted according to a user's preferences.

As discussed above, the ability of a dental instrument to "activate" (e.g., to turn on a motor) when exposed to the environment in which it is used (e.g., an electrolyte solution in the mouth) can obviate the need for an "on/off" switch or button, creating a simplified operation.

Another embodiment of a motorized device activated when conducting elements 7 are exposed to an electrolyte solution is shown in FIG. 2. A reservoir 44 is provided in handle 1 for storing an active agent. Conducting elements 7 are used to activate a pump 46, which causes a predetermined quantity of the active agent to be delivered from reservoir 44 through a channel 48 leading to a plurality of outlets 50 located in head 5. An exemplary delivery system for an active agent is described in copending Application Ser. No. 11/457,086, the entire disclosure of which is incorporated herein. Other examples of motorized devices that can be activated upon exposure of conducting elements 7 to an electrolyte solution will become readily apparent to those skilled in the art, given the benefit of this disclosure.

In view of the above, it will be seen that several advantages may be achieved and other advantageous results may be obtained. As various changes could be made in the above oral care instruments without departing from the scope of the present disclosure, it is intended that all matter contained in this application shall be interpreted as illustrative only and not limiting in any way the scope of the appended claims.

We claim:
1. A motorized toothbrush comprising:
a head carrying cleaning elements on an upper surface thereof;
a handle configured to connect to a power source;
a neck extending between the head and the handle;
at least one pair of electrical conducting elements including an anode and a cathode, the anode and the cathode being disposed in respective bores spaced from each other in a lower surface of the neck facing away from the upper surface of the head, a portion of the anode and a portion of the cathode exposed to an exterior environment of the toothbrush; and
a motorized device;

wherein the motorized device is activated upon contact of the anode and the cathode to an electrolyte solution, the electrolyte solution extending between the cathode and the anode.

2. The toothbrush of claim 1, wherein the motorized device causes movement of the head.

3. The toothbrush of claim 1, wherein the electrolyte solution completes an electrical circuit with the power source.

4. The toothbrush of claim 1, further comprising electrical connections operably connected to the motorized device.

5. The toothbrush of claim 4, wherein the electrical connections are operably connectable to the power source.

6. The toothbrush of claim 1, wherein the motorized device activates and causes vibration or rotation of the cleaning elements, upon exposure of the toothbrush to the electrolyte solution.

7. The toothbrush of claim 1, wherein the toothbrush is switchless or buttonless.

8. The toothbrush of claim 1, further comprising electrical connections operably connected to the motorized device, and a switch operably connected to at least one of the electrical connections and the anode and cathode to prevent electrical communication between the power source and the motorized device even when the electrolyte solution is contacting and extending between the anode and the cathode or to complete an electrical circuit even without the electrolyte solution contacting and extending between the anode and the cathode.

9. The toothbrush of claim 8, wherein the switch has at least three settings associated with interruption of the electrical circuit, completion of the electrical circuit, and conditional completion of the electrical circuit upon the electrolyte solution contacting and extending between the anode and the cathode.

10. The toothbrush of claim 1, further comprising a sensing device operably connected to the anode and the cathode.

11. The toothbrush of claim 10, wherein the sensing device measures conductance between the anode and the cathode.

12. The toothbrush of claim 1, wherein the motorized device activates upon the electrolyte solution that contacts and extends between the anode and the cathode having a threshold conductivity.

13. The toothbrush of claim 12, wherein the threshold conductivity is based on a conductivity of saliva.

14. The toothbrush of claim 13, wherein the threshold conductivity is based on the conductivity of saliva having one or more additional amounts of dissolved ions selected from the group consisting of calcium, phosphate, fluoride, peroxide, and mixtures thereof.

15. The toothbrush of claim 1, wherein the motorized device activates for a minimum predetermined duration upon exposure of the toothbrush to the electrolyte solution.

16. The toothbrush of claim 1, wherein the handle includes a cavity and further comprising a battery insertable into the cavity.

17. The toothbrush of claim 16, wherein the cavity contains an electrically conductive sleeve which is open to the rear and closeable by a rear cover.

18. The toothbrush of claim 1, further comprising a switch that is activated to complete an electrical circuit with a power source based on a conductivity or resistivity of the electrolyte solution.

19. The toothbrush of claim 1, wherein the motorized device is a pump operatively connected to a reservoir and configured to deliver an active agent from the reservoir to outlets in the head.

20. A motorized toothbrush comprising:
a head carrying cleaning elements on an upper surface thereof;
a handle;
a neck extending between the head and the handle;
a power source contained within the handle;
a motorized device operably connected to the power source and operably connected to the head;
electrical conducting elements comprising an anode and a cathode operably connected to the power source and the motorized device, the anode and the cathode disposed in respective bores spaced from each other in a lower surface of the neck facing away from the upper surface of the head, a portion of the anode and a portion of the cathode exposed to an exterior environment of the toothbrush; and
a switch operably connected to at least one of the electrical conducting elements and the power source;
wherein the motorized device is activated upon contact of the anode and the cathode to an electrolyte solution having a threshold conductivity, the electrolyte solution extending between the cathode and the anode.

* * * * *